(12) United States Patent
Pagel et al.

(10) Patent No.: US 9,138,549 B2
(45) Date of Patent: Sep. 22, 2015

(54) INSUFFLATOR

(75) Inventors: Lienhard Pagel, Klockenhagen (DE); Stefan Gabmann, Rostock (DE); Johannes Tschepe, Berlin (DE)

(73) Assignees: MGB ENDOSKOPISCHE GERAETE GMBH BERLIN, Berlin (DE); UNIVERSITAET ROSTOCK, Rocstock (DE)

( * ) Notice: Subject to any disclaimer, the term of this patent is extended or adjusted under 35 U.S.C. 154(b) by 966 days.

(21) Appl. No.: 13/146,500

(22) PCT Filed: Jan. 29, 2010

(86) PCT No.: PCT/EP2010/051095
§ 371 (c)(1),
(2), (4) Date: Jul. 27, 2011

(87) PCT Pub. No.: WO2010/086412
PCT Pub. Date: Aug. 5, 2010

(65) Prior Publication Data
US 2011/0308326 A1  Dec. 22, 2011

(30) Foreign Application Priority Data
Jan. 29, 2009  (DE) .......................... 10 2009 007 393

(51) Int. Cl.
*A61M 13/00*  (2006.01)
*H05K 1/02*  (2006.01)
(Continued)

(52) U.S. Cl.
CPC ............ *A61M 13/003* (2013.01); *H05K 1/0272* (2013.01); *A61B 17/3474* (2013.01); *H05K 1/181* (2013.01); *H05K 2201/10151* (2013.01)

(58) Field of Classification Search
CPC ... A61B 1/015; A61B 17/3474; A61M 13/00; A61M 2205/3331; A61M 2205/3344; A61M 13/003
USPC ..................... 600/560, 561; 604/26
See application file for complete search history.

(56) References Cited

U.S. PATENT DOCUMENTS

| 5,423,741 | A | 6/1995 | Frank |
| 6,299,592 | B1 | 10/2001 | Zander |

(Continued)

FOREIGN PATENT DOCUMENTS

| DE | 197 39 722 A1 | 4/1999 |
| EP | 1 596 455 A1 | 11/2005 |

(Continued)

OTHER PUBLICATIONS

International Search Report prepared by the European Patent Office on May 7, 2010, for International Application No. PCT/EP2010/051095.

*Primary Examiner* — Max Hindenburg
(74) *Attorney, Agent, or Firm* — Sheridan Ross P.C.

(57) ABSTRACT

The invention relates to an insufflator with a supply connection (22) and a delivery connection (14) and a pressure and flow measuring device arranged between said connections (14, 22) for determining measured quantities characterizing a gas pressure at a delivery connection and a gas volume flow at the delivery connection. The pressure and flow measuring device comprises a multilayer board (20) which comprises on its interior at least one flow channel (26) that is connected at its input to the supply connection (22) and at its output (8) to the delivery connection (14). Arranged on the board (20) are pressure measurement sensors (32, 34) and electronic components (4, 6) for the wiring of the pressure measurement sensors. The pressure measurement sensors are each directly connected to the flow channel (26) via a corresponding opening of a board layer that otherwise tightly covers the flow channel (26) and are designed to provide an output value representing a static pressure at the point of the respective opening.

11 Claims, 2 Drawing Sheets

Figure 1:
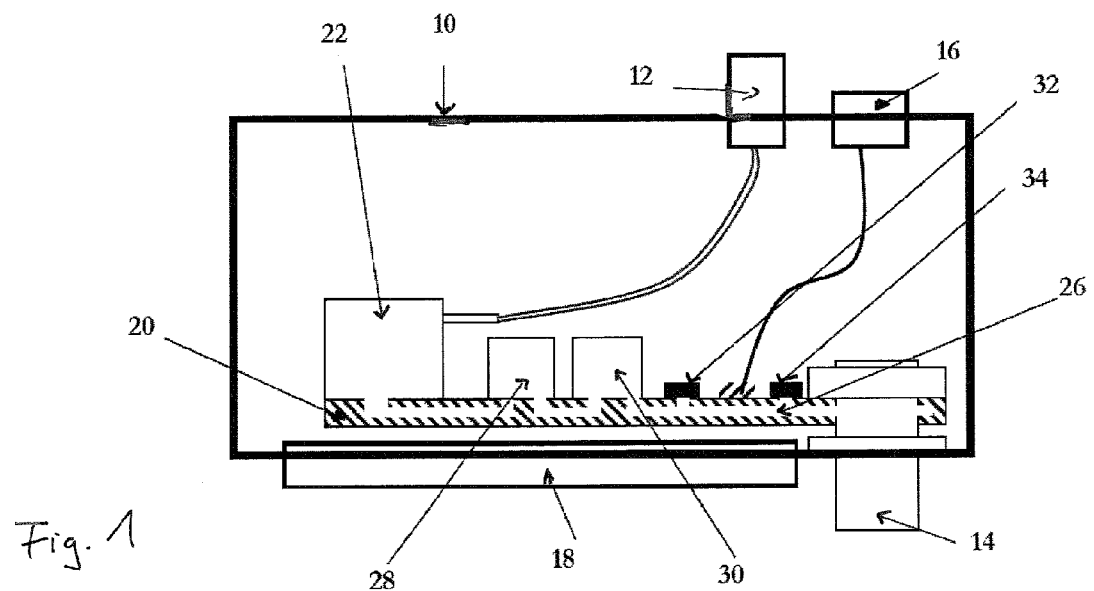

(51) Int. Cl.
    *A61B 17/34*    (2006.01)
    *H05K 1/18*    (2006.01)

(56)    References Cited

U.S. PATENT DOCUMENTS 7,641,668 B2 *   1/2010   Perry et al. .................... 606/192
7,993,298 B2 *   8/2011   Heath ............................. 604/26
8,257,297 B2 *   9/2012   Mantell ........................... 604/26
8,269,638 B2 *   9/2012   Lloyd et al. .................... 340/603
8,734,381 B2 *   5/2014   Noda et al. ...................... 604/26

FOREIGN PATENT DOCUMENTS

WO    WO 94/01154    A1    1/1994
WO    WO 2007/114687 A1    10/2007

* cited by examiner

INSUFFLATOR

The invention relates to an insufflator.

Insufflators are used in laparoscopy (endoscopic abdominal surgery) and serve to give an operator an unobstructed view of the operating field in the abdomen through an endoscope by feeding carbon dioxide ($CO_2$) into the abdomen. To do this, $CO_2$ gas is insufflated into the abdomen through a so-called Veress cannula or a trocar at a maximum pressure of 30 $mm_{Hg}$. As a result of the rising internal pressure, the abdominal wall (peritoneum) is lifted up and the desired hollow space is formed in the abdomen, which enables the endoscopic observation of the operating field. Such $CO_2$ insufflators are known in principle.

Two basic principles are known from the prior art for the designing of insufflators.

According to the first principle, the pneumatic components are firmly screwed to the housing of the device. The pneumatic components are connected by tubes. The pneumatic components are connected to the electronics (e.g., for valves and pressure sensors) by cables. The manufacturing costs are high. The tubes have to be cut to size, put in place and secured. The cables have to be assembled. These activities cannot be carried out by machine. Due to the manual production and the monotonous procedure, the error frequency is high.

According to the second principle, the pneumatic components are integrated in a block. All of the pneumatic connections are realized in this block. The pneumatic components are screwed onto this block. There is little or no need for the provision of tubes. The pneumatic components are connected to the electronics by cables. By virtue of the second principle, the provision of tubes—with all of its possibilities for error—is eliminated.

Taking known insufflators as a starting point, it is the object of the invention to provide an improved insufflator which, as a result of its simple design, can be manufactured economically, is reliable and also permits sufficiently high volumes of flow.

According to the invention, this object is achieved by an insufflator which has, in the usual manner, a supply connection and a delivery connection and a pressure and flow measuring device arranged between said connections. The pressure and flow measuring device is designed for determining the gas pressure at the delivery connection and the gas volume flow at the delivery connection. According to the invention, the pressure and flow measuring device comprises a multilayer board having on its interior at least one flow channel that is connected at its input to the supply connection and at its output to the delivery connection. Pressure measurement sensors and electronic components for the wiring of the pressure measurement sensors are arranged on the board. Each of the pressure measurement sensors is directly connected to the flow channel via a corresponding opening with a board layer that otherwise tightly covers said flow channel and is designed to provide an output value representing a static pressure at the point of the respective opening.

One advantage of the invention is that the board which encloses the flow channel furthermore matches circuit boards such as those that are used in known devices for electronic components, so the electronic components are brought together into an assembly though the board with the otherwise separately embodied fluid elements of an insufflator. This advantageously leads to a monolithic integration of electronics and fluidics in a common base. As a result, the otherwise usual provision of tubes and wiring is eliminated. This, in turn, simplifies the manufacturing process and increases reliability. The manufacturing process can also be easily automated. Finally, the insufflator can have an extremely compact construction, even in comparison to known insufflators. Through the use of circuit board material as the base for the board of the insufflator according to the invention, costs can be further reduced. Circuit boards and the related technology are widely used and are very cost-effective.

Accordingly, in a preferred embodiment of the insufflator, all of the boards in the multilayer board are conventional epoxy resin circuit boards, for example with a material identifier of FR4.

However, today's known standard circuit board technology is not capable of performing fluid functions. This hitherto prevailing limitation is overcome by a board which has on its interior a flow channel and can be constructed, for example, as a multilayer board.

This enables—as mentioned previously—a monolithic construction through automatic manufacture. The entire $CO_2$ insufflator, which can also include the power supply, is manufactured through automation on the basis of a multilayer board. All that is then required are installation into a clinically suitable device, calibration, and the final check.

The simplification achieved in this way can lead to savings on the order of magnitude of up to 70% compared to the manufacturing costs of today's insufflators. Preferably, the supply connection and the delivery connection as well as the pressure sensors are each adhered to the multilayer board in such a manner that the supply connection, the delivery connection and the pressure sensors are connected to the flow channel formed by the hollow space of the board and hence to each other. Through the adhering of the fluid components (supply connection, delivery connection and pressure sensors) to the board, it is possible to connect these components to the board in a gas-tight and secure manner. One suitable adhesive is, for example, the adhesive that is also used to fix common electronic components to the board prior to the soldering of these components. This enables particularly simple manufacture, which simultaneously leads to a high-quality result.

Alternatively, the supply connection and the delivery connection as well as the pressure sensors are each connected to the multilayer board by means of screws or other fastening means.

The pressure sensors are preferably arranged on the multilayer board in such a manner that they are adhered rearwardly on the board and are therefore fluidly connected to the flow channel. Consequently, the pressure sensors are loaded rearwardly with pressure during operation of the insufflator. The term "rearward" is to be understood here such that the opening of a common differential pressure sensor that is normally in direct contact with the ambient air is connected to the flow channel in the preferred embodiment, whereas the other opening usually facing the pressure to be measured is open toward the ambient pressure. Alternatively, the pressure sensors can also be arranged the other way around.

Preferably, the pressure sensors are further soldered with their electrical connectors to the board. For this purpose, the board preferably has electrical wiring paths. This provides for another secure mechanical and electrical connection of these pressure sensors to the board and the other electrical components of an insufflator. These other components are likewise preferably soldered to the board and connected to each other and to the pressure sensors by means of wiring paths.

Moreover, one or more valves are preferably arranged on the board such that they are fluidly connected to the flow channels and are loaded with pressure and flow during operation of the insufflator. The valves have electrical connectors that are preferably soldered to wiring paths of the board.

In a preferred embodiment of the insufflator, the flow channel is formed by a hollow space in the multilayer board, which is formed such that it has a cross section that acts as a flow restrictor and enables volume flow measurement according to the principle of a pneumotachograph.

For volume flow measurement, the flow restrictor has, in a preferred embodiment, the following dimensions: channel length of approximately 60 mm, channel height of approximately 1 mm and a channel width of approximately 6 mm.

Preferably, pressure sensors are arranged at the input and at the output of the section of the hollow space acting as a flow restrictor, each of which is connected to electronic components that are designed to determine a difference between the static pressure at the input of the section of the hollow space acting as a flow restrictor and the static pressure at the output of the section of the hollow space acting as a flow restrictor.

Accordingly, the insufflator is preferably designed to implement flow regulation through pressure regulation. For this purpose, the embodiment of the insufflator is designed to operate according to a low-pressure principle in which the insufflation pressure is equal to a nominal pressure which generally corresponds to a theoretical maximum pressure in the abdomen. Due to a drop in pressure over the inlet and along a wall of a tube leading to the abdomen, there is actually a lower pressure in the abdomen than the nominal pressure. This method usually constitutes a continuous method.

In another embodiment, the insufflator is designed to function according to an overpressure principle in which the insufflation pressure is set incrementally higher than the nominal pressure, a measurement of an intraabdominal pressure being performed here cyclically during pauses in which the insufflation pressure and the volume flow are each set to an amount of about zero. This overpressure method usually constitutes an intermittent method.

In a preferred embodiment, the insufflator is designed to feed the gas into the patient's body in accordance with a quasi-continuous method known from European Patent Application EP 1 352 669 A1. Explicit reference is made to this publication, particularly to the sample embodiments according to FIGS. 4 and 5. According to this, the insufflator is preferably designed to execute the insufflation of the gas in dependence on a presettable target pressure in the body and the volume flow, to insufflate the gas with overpressure on greater than the target pressure if the actual pressure in the patient's body is less than the target pressure, to reduce the volume flow during insufflation with overpressure cyclically and down to the target pressure or a lower nominal pressure in order to determine a difference and a control between target pressure and actual pressure in the body and to use for further insufflation the value of the measured volume flow at the target pressure or nominal pressure as a controlled variable between target pressure and actual pressure in the body. The flow channel on the interior of the multilayer board is preferably formed by a hollow space which has a clearance height (in the direction of thickness of the boar) of 1 mm and a clearance width of 1-8 mm. It has turned out that such a flow channel, for one thing, is easy to realize with the aid of a multilayer board and, for another, permits a volume flow of greater than 40 l/min of gaseous $CO_2$. Accordingly, an insufflator is also preferred which is designed for a $CO_2$ gas volume flow of greater than 40 l/min.

Moreover, the insufflator is preferably designed for an output pressure (which corresponds to the abdominal pressure) of up to 30 $mm_{Hg}$. This corresponds approximately to a pressure of 4 kPa.

A ventilator, a monitor or patient monitoring device and a blood pressure measuring device constitute further aspects of the invention. The ventilator, monitor or patient monitoring device and blood pressure measuring device each have, in the usual manner, a supply connection and a delivery connection and a pressure and flow measurement device arranged between these connections. The pressure and flow measuring device is designed to determine a gas pressure at the supply connection and a gas volume flow at the delivery connection. According to the invention, the pressure and flow measuring device comprises a multilayer board which has on its interior at least one flow channel that is connected at its input to the supply connection and at its output to the delivery connection. Arranged on the board are pressure measurement sensors as well as electronic components for wiring the pressure measurement sensors. The pressure measurement sensors are each directly connected to the flow channel through a corresponding opening to the flow channel with an incidentally tightly covering board layer and designed to provide an output value representing a static pressure at the point of the respective opening.

The ventilator, the monitor or patient monitoring device and the blood pressure measuring device share the advantages of the insufflator according to the invention to the greatest possible extent.

The object of the present invention is also a method for manufacturing an insufflator which comprises the steps:
preparation of a multilayer board with integrated flow channel;
equipping the board with fluid components through adhesion of the fluid components;
equipping the board with electrical components by soldering them on.

The method step of equipping the board with fluid components preferably comprises the application of adhesive by means of a dispenser. Preferably, this application of adhesive is done in the manner that is usual in the equipping of electronic components in SMD (Surface Mounted Device) technology.

Further advantageous embodiments of the insufflator according to the invention follow from the following description of a sample embodiment.

The invention will now be explained in further detail on the basis of a sample embodiment with reference to the figures.

Figure 2:
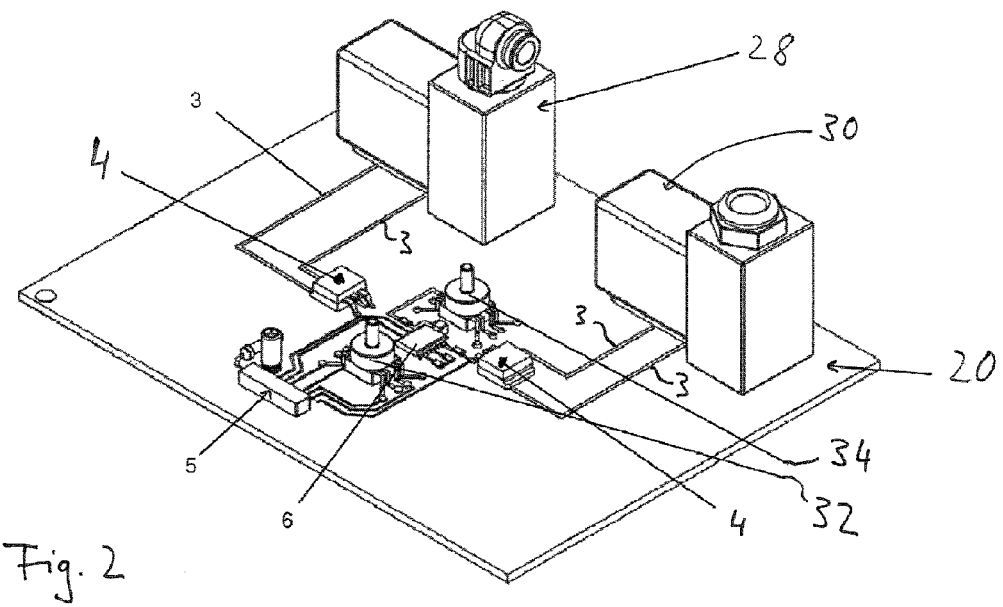
Figure 3:
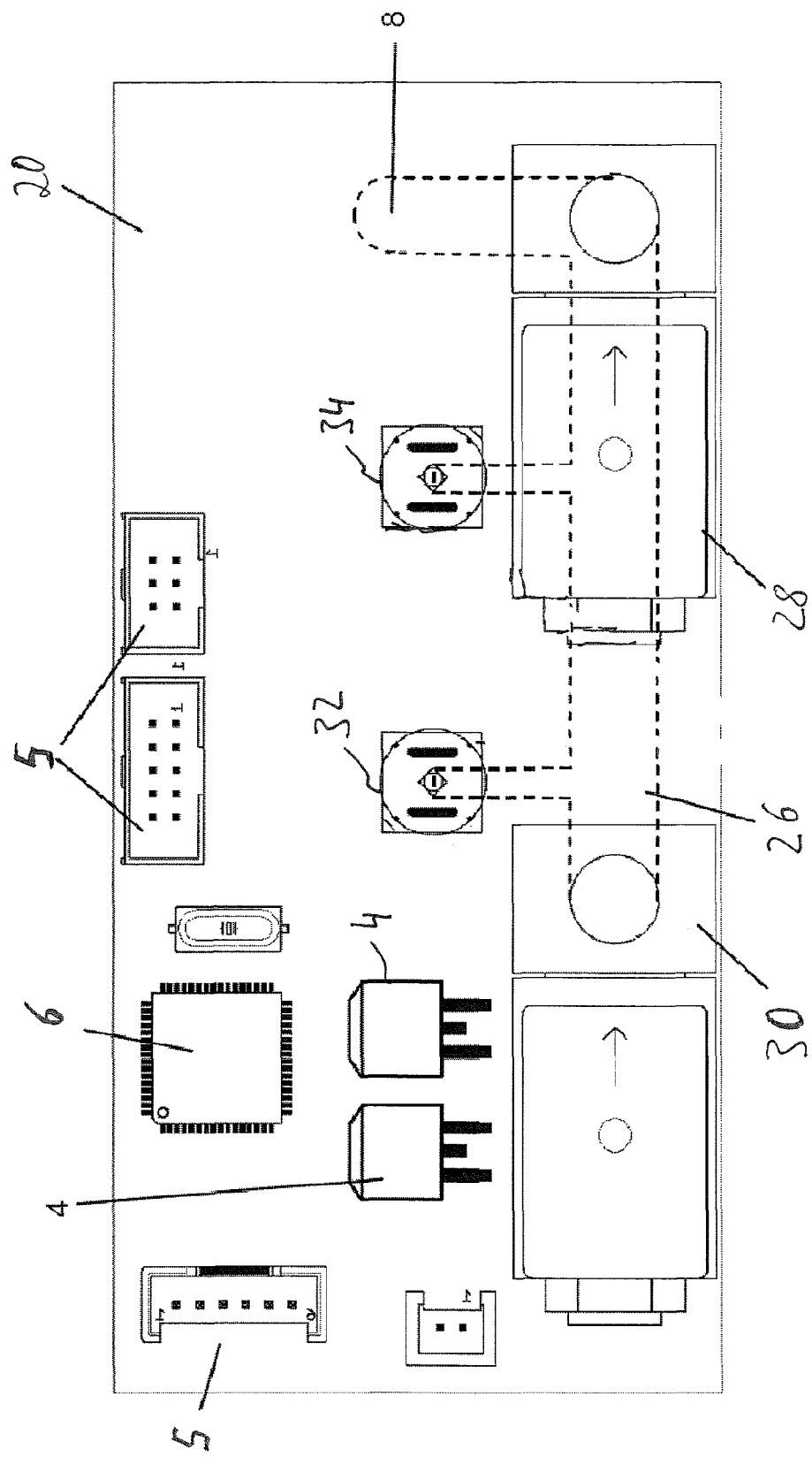

FIG. 1: shows a schematic cross section through an insufflator according to the invention;

FIG. 2: shows a schematic representation of a top view of a particular multilayer board of the insufflator according to the invention; and FIG. 3: shows a schematic representation of the primary layout of the board from FIG. 2.

Schematically indicated in FIG. 1 is a housing 10 of an insufflator on which a $CO_2$ connection 12 is provided for connection to a source for gaseous $CO_2$ as well as a delivery connection 14 to which a tube for insertion into the abdomen of a patient is connected. Moreover, the insufflator according to FIG. 1 has an electrical power supply 16 and a control panel 18.

The core piece of the insufflator from FIG. 1 is a multilayer board 20 onto which a supply connection 22 and the delivery connection 14 are adhered in a gas-tight manner. The supply connection 22 is connected to the $CO_2$ connection 12 through a corresponding tube 11.

The board 20 is multilayered and has on its interior hollow spaces which form a multipart flow channel 26. The supply connection 22 and the delivery connection 14 are fluidly connected to this flow channel 26. Moreover, electrical and electronic components of the insufflator are mounted on the outside of the board 20 in addition to valves 28 and 30 and pressure sensors 32 and 34. The valves 28 and 30 and the pressure sensors 32 and 34 are also adhered to the board 20 in a gas-tight manner. The pressure sensors 32 and 34 are differential pressure sensors which are adhered rearwardly to the board 20 in a gas-tight manner.

The various sections of the flow channel 26 on the interior of the board 20 have a clearance height of 1 mm and a clearance width of between 1 mm and 8 mm.

The insufflator permits a gas volume flow of $CO_2$ of up to 44 l/min. It is designed for an intra-abdominal pressure of 1 to 30 $mm_{Hg}$. Intermittent gas flow is possible through the valves 28 and 30.

FIG. 2 shows a schematic representation of the core piece of the insufflator from FIG. 1, namely the multilayer board 20 with the electronic and fluid components mounted thereon which are necessary for the insufflator shown for the sake of example. These are the valves 28 and 30, power electronic components 4 that are connected to the valves 28 and 30 through wiring paths 3, the pressure sensors 32 and 34, a plug connector 5 for connecting to the electrical network 16, a valve control, a sensor signal processor, a microcontroller 6, buttons and displays. The flow channels on the interior of the multilayer board are not shown in FIG. 2. They constitute the fluid connection between the supply connection 22 and the delivery connection 14 as well as the valves 28 and 30 and pressure sensors 32 and 34, which are also attached as pneumatic (fluid) components to the board 20. The fluid components are arranged here such that they have fluid contact both with the flow channels arranged on the interior of the board 20 and electrical contact to the electrical and electronic components 4 and 6 of the insufflator. This two-fold use of the board 20 enables a compact and economical insufflator design.

FIG. 3 shows a schematic representation of the layout of the board 20 including the flow channel 26, the power electronic components 4, the microcontroller 6, a plurality of plug connectors 5, the mounted valves 28 and 30, the pressure sensors 32 and 34 and a flow channel outlet 8 which leads to the delivery connection 14 not shown in FIG. 3. This multilayer board 20 constitutes a significant innovation of the insufflator according to the invention. Crucial for this are the hollow spaces on the interior of the board 20 which are created as a result of individual circuit boards being adhered together with a suitable layout over a large surface and in a gas-tight manner. Such a multilayer board differs from known standard technologies for the manufacture of multilayer circuit boards, since the individual circuit boards must first be coated completely with a suitable adhesive and then pressed.

Known adhesion techniques of known multilayer circuit boards differ from the multilayer board according to the invention because they are usually not adhered together in a gas-tight manner, whereas this is the case with the multilayer board 20 according to the invention.

LIST OF REFERENCE SYMBOLS 3 wiring paths
4 power electronic components
5 plug connector
6 microcontroller
8 outlet of the flow channel 26
10 housing of an insufflator
11 tube
12 $CO_2$ connection
14 delivery connection
16 power supply
18 control panel
20 multilayer board
22 supply connection
26 flow channel
28,30 valves
32,34 pressure sensors

The invention claimed is:

1. An insufflator with a supply connection and a delivery connection and a pressure and flow measuring device arranged between said connections for determining measured quantities characterizing a gas pressure at the delivery connection and a gas volume flow at the delivery connection,
    characterized in that the pressure and flow measuring device comprises a board which comprises on its interior at least one flow channel that is connected at its input to the supply connection and at its output to the delivery connection,
    wherein pressure measurement sensors and electronic components for the wiring of the pressure measurement sensors are arranged on the board, of which each of the pressure measurement sensors is connected directly to the at least one flow channel via a corresponding opening of a board layer that otherwise tightly covers the flow channel and is designed to provide an output value representing a static pressure at the point of the respective opening.

2. The insufflator as set forth in claim 1, characterized in that the supply connection and the delivery connection as well as the pressure sensors are each adhered in a gas-tight manner to the board layer covering the flow channel such that the supply connection, the delivery connection and the pressure sensors are connected pneumatically to each other through the flow channel.

3. The insufflator as set forth in claim 2, characterized in that the pressure sensors are rearwardly and fluidly connected to the flow channel and loaded rearwardly with pressure during operation of the insufflator.

4. The insufflator as set forth in claim 1, characterized in that the pressure measurement sensors are soldered to the board.

5. The insufflator of claim 1, further comprising at least one valve that is fluidly connected to the at least one flow channel such that it is loaded with pressure during operation of the insufflator.

6. The insufflator of claim 5, wherein the at least one valve includes electrical connections that are soldered to the board.

7. The insufflator of claim 1, characterized in that the flow channel is formed by a hollow space in the board which is formed such that it has a section that acts as a flow restrictor and enables volume flow measurement according to the principle of a pneumotachograph.

8. The insufflator of claim 1, characterized in that pressure sensors are arranged at the input and at the output of the section of the hollow space acting as a flow restrictor, each of which is connected to electronic components that are designed to determine a difference between the static pressure at the input of the section of the hollow space acting as a flow restrictor and the static pressure at the output of the section of the hollow space acting as a flow restrictor.

9. The insufflator of claim 1, characterized in that the flow channel has a clearance height of 1 mm and a clearance width of 1 mm to 8 mm.

10. The insufflator of claim 1, characterized in that the insufflator is designed for a gas volume flow of greater than 40 liters per minute.

11. The insufflator of claim 1, characterized in that the insufflator is designed for an input gas pressure of up to at least 30 mmHg.

\* \* \* \* \*